United States Patent [19]

Pande

[11] Patent Number: 5,510,381
[45] Date of Patent: Apr. 23, 1996

[54] METHOD OF TREATMENT OF MANIA AND BIPOLAR DISORDER

[75] Inventor: Atul C. Pande, Ann Arbor, Mich.

[73] Assignee: Warner-Lambert Company, Morris Plains, N.J.

[21] Appl. No.: 440,570

[22] Filed: May 15, 1995

[51] Int. Cl.⁶ ............... A61K 31/195; A61K 31/215
[52] U.S. Cl. ............ 514/561; 514/529; 514/530
[58] Field of Search ................. 514/561, 529, 514/530

[56] References Cited

U.S. PATENT DOCUMENTS

| | | | |
|---|---|---|---|
| 4,024,175 | 5/1977 | Satzinger et al. | 260/468 J |
| 4,087,544 | 5/1978 | Satzinger et al. | 424/305 |
| 5,025,035 | 6/1991 | Wallace | 514/530 |
| 5,084,479 | 1/1992 | Woodruff | 514/530 |

OTHER PUBLICATIONS

Co-pending U.S. patent application No. 08/281,285, filed Jul. 27, 1994.

*Primary Examiner*—Raymond Henley, III
*Assistant Examiner*—William R. A. Jarvis
*Attorney, Agent, or Firm*—Elizabeth M. Anderson

[57] ABSTRACT

The present invention is a novel therapeutic use of gabapentin, its derivatives, and the pharmaceutical salts thereof. The compounds are useful in the treatment of mania in all its various forms whether acute or chronic, single or recurrent, and whether or not it is associated with depression. The invention further includes the treatment of bipolar disorder.

8 Claims, No Drawings

METHOD OF TREATMENT OF MANIA AND BIPOLAR DISORDER

BACKGROUND OF THE INVENTION

U.S. Pat. Nos. 4,024,175 and 4,087,544, which are incorporated herein by reference, teach cyclic amino acids of formula

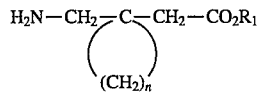

wherein $R_1$ is hydrogen or lower alkyl and n is an integer of from 4 to 6 and the pharmaceutically acceptable salts thereof.

The compounds disclosed in the above United States patents are useful for the therapy of certain cerebral diseases, for example, they can be used for the treatment of certain forms of epilepsy, faintness attacks, hypokinesia, and cranial traumas. Additionally, they bring about an improvement of cerebral functions and thus are useful in treating geriatric patients. Particularly valuable is 1-(aminomethyl)-cyclohexane-acetic acid (gabapentin).

U.S. Pat. No. 5,084,479 teaches the compounds of the above formula for therapeutic use in neurodegenerative disorders such as Alzheimer's, Huntington's, Parkinson's, and Amyotrophic Lateral Sclerosis. It also teaches the use of the compounds in the treatment of acute brain injury such as stroke, head trauma, and asphyxia.

U.S. Pat. No. 5,025,035 teaches the use of the compounds of the above formula for depression.

U.S. patent application Ser. No. 08/281285 teaches the use of the compounds of the above formula to treat anxiety and/or panic disorders.

There is no disclosure in the above references to make obvious the present invention of novel uses of the compounds of U.S. Pat. No. 4,024,175 to treat mania and/or bipolar disorder.

SUMMARY OF THE INVENTION

The present invention relates to novel therapeutic uses of a known compound, gabapentin, its derivatives, and pharmaceutically acceptable salts. The invention concerns a method for treating the symptoms of mania in a human in need of such treatment. This method includes, but is not limited to the treatment of mania in all its various forms whether acute or chronic, single or recurrent episode, and associated with depression or not. The invention further includes the preventive treatment of bipolar disorder in persons predisposed to this disorder.

Episodes of acute mania are characterized by elevated or irritable mood, disturbed sleep, grandiosity, increased motor activity, pressured thinking, distractibility and poor concentration, impaired judgement, and sometimes psychotic symptoms. The irritability can lead to outbursts of angry or aggressive behavior. Often the episodes are preceded by a period of disturbed sleep. The distractibility makes the patient move endlessly from one activity to another often to the detriment of their physical, occupational, and social well-being. The impact of these behaviors is further aggravated by the lapses of judgement and poor decision-making that is characteristic of this illness.

Episodes of mania occur in patients who suffer from bipolar disorder which is an illness characterized by alternating cycles of depression and mania. This disorder is distinct from the more common form of depression, called Major Depressive Disorder, in which patients only experience recurrent episodes of depression but no mania. Bipolar disorder can be diagnosed by the clinical evaluation of patients using the criteria specified in the Diagnostic and Statistical Manual (DSM-IV) of the American Psychiatric Association. In this nomenclature system, bipolar disorder is subsumed under the broader class of Mood Disorders and is clearly distinguished from the Anxiety Disorders and from Organic Mental Disorders.

In studies of epilepsy, gabapentin has been noted to reduce anger and irritability, enhance concentration, and improve decision-making abilities. These effects will be beneficial in the symptomatic treatment of patients suffering from mania who exhibit irritability, distractibility, and poor judgement. This is a novel use for gabapentin which would not be obvious to a medical practitioner of ordinary skill.

In one study gabapentin has also been found to enhance delta-wave (deep) sleep. This effect will be beneficial in acute mania and will also lead to reducing the risk for onset of a new episode of mania in a predisposed individual. Thus, the prophylactic use of gabapentin for bipolar disorder is also taught.

DETAILED DESCRIPTION

The present invention relates to novel methods of treating mania and/or bipolar disorder in a mammal in need of such treatment. The treatment comprises administering in unit dosage form an effective amount of a compound of formula

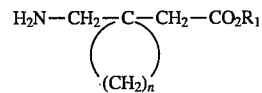

wherein $R_1$ is hydrogen or a lower alkyl and n is 4, 5, or 6 or a pharmaceutically acceptable salt thereof. The term lower alkyl includes straight or branched chain alkyl groups of up to 8 carbon atoms.

Preferred compounds of Formula I above include but are not limited to 1-aminomethyl-1-cyclohexane-acetic acid, ethyl 1-aminomethyl-1-cyclohexane-acetate, 1-aminomethyl-1-cycloheptane-acetic, acid 1-aminomethyl-1-cyclopentane-acetic acid, methyl 1-aminomethyl-1-cyclohexane-acetate, n-butyl 1-aminomethyl-1-cyclohexane-acetate, methyl 1-aminomethyl-1-cycloheptane-acetate, n-butyl 1-aminomethyl-1-cycloheptane-acetate, toluene sulfonate, 1-aminomethyl-1-cyclopentane-acetate, benzene-sulfonate, and n-butyl 1-aminomethyl-1-cyclopentane-acetate.

The most preferred compound is 1-aminomethyl-cyclohexane acetic acid (gabapentin).

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present.

Routes of administration of the subject compound or its salts are oral or parenteral. For example, a useful intravenous dose is between 5 and 50 mg and a useful oral dosage is between 20 and 200 mg. The dosage is within the dosing range used in epilepsy treatment or as would be with the needs of the patient as described by the physician.

A unit dosage form of the instant invention may also comprise other compounds useful in the therapy of neurodegenerative diseases.

The advantages of using the compounds of Formula I, especially gabapentin, in the instant invention include the relatively nontoxic nature of the compound, the ease of preparation, the fact that the compound is well-tolerated, and the ease of IV administration of the drug. Further, the drug is not metabolized in the body.

The subjects as used herein are mammals, including humans.

The usefulness of compounds of Formula I above and the salts thereof as agents for mania in all its various form and in the preventative treatment of bipolar disorder is demonstrated in its effects on the mental functions of patients. These effects were observed during epilepsy clinical trial. See Table 1 below wherein the effects beneficial to patients with bipolar disorder are presented.

TABLE 1

| Patient No. | Effect |
| --- | --- |
| 1 | More relaxed |
| 2 | More socially responsive, better concentration |
| 3 | More sharp cognitively, more relaxed. Decreased confusion, increased comprehension |
| 4 | Less nervous energy, more serene |
| 5 | More relaxed |
| 6 | Less insomnia |

TABLE 1-continued

| Patient No. | Effect |
| --- | --- |
| 7 | Thinking is clearer |
| 8 | Psychic improvement, more present, more relaxed |
| 9 | Able to think more clearly |
| 10 | More clear than before |
| 11 | More relaxed |
| 12 | More relaxed and somehow better |
| 13 | Feels better, has not been so impulsive |
| 14 | Alertness and speech have improved |
| 15 | More alert and able to concentrate better |
| 16 | More clear headed, memory has improved |

I claim:

1. A method for treating the symptoms of mania in a mammal in need of said treatment which comprises administering a therapeutically effective amount of a compound of formula

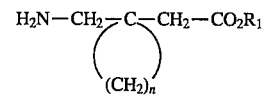

or a pharmaceutically acceptable salt thereof wherein $R_1$ is hydrogen or lower alkyl and n is an integer of from 4 to 6 in unit dosage form.

2. A method according to claim 1 wherein the mania is acute.

3. A method according to claim 1 wherein the mania is chronic.

4. A method according to claim 1 wherein the mania is a single episode.

5. A method according to claim 1 wherein the mania is recurring.

6. A method according to claim 1 wherein gabapentin is administered.

7. A method for treating bipolar disorder in a mammal in need of said treatment which comprises administering a therapeutically effective amount of a compound of formula

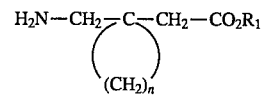

or a pharmaceutically acceptable salt thereof wherein $R_1$ is hydrogen or lower alkyl and n is an integer of from 4 to 6 in unit dosage form.

8. A method according to claim 7 wherein the compound administered is gabapentin.

* * * * *